United States Patent
Takata et al.

(10) Patent No.: US 6,599,933 B2
(45) Date of Patent: Jul. 29, 2003

(54) TOCOTRIENOL DERIVATIVE, PROCESS FOR PRODUCING THE SAME AND γ-CEHC DELIVERING AGENT

(75) Inventors: Jiro Takata, 19-14, Ikimatsudai, 1-chome, Nishi-ku, Fukuoka-shi Fukuoka (JP), 819-0044; Takeshi Fukushima, Tokyo (JP); Kazuhiro Imai, 15-18, Daita 6-chome, Setagaya-ku, Tokyo (JP), 155-0033; Yoshiharu Karube, Fukuoka (JP); Kazuhisa Matsunaga, Fukuoka (JP); Michihiro Fujiwara, Fukuoka (JP); Akihiro Hattori, Tokyo (JP); Ryoji Hidaka, Fukuoka (JP); Katsunori Iwasaki, Fukuoka (JP); Kenichi Mishima, Fukuoka (JP); Shizuko Kobayashi, Tokyo (JP)

(73) Assignees: Jiro Takata, Fukuoka (JP); Kazuhiro Imai, Tokyo (JP); Kenko Corporation, Tokyo (JP)

( * ) Notice: Subject to any disclaimer, the term of this patent is extended or adjusted under 35 U.S.C. 154(b) by 0 days.

(21) Appl. No.: 09/797,180

(22) Filed: Mar. 2, 2001

(65) Prior Publication Data

US 2003/0027857 A1 Feb. 6, 2003

(30) Foreign Application Priority Data

Sep. 5, 2000 (JP) .................................. 2000-268885

(51) Int. Cl.$^7$ .............................................. A01N 43/16
(52) U.S. Cl. ..................... 514/458; 549/407; 549/408
(58) Field of Search ................. 549/407, 408; 514/458

(56) References Cited

U.S. PATENT DOCUMENTS

| | | | |
|---|---|---|---|
| 5,604,450 A | 2/1997 | Borkar et al. ................. | 326/82 |
| 5,869,704 A | 2/1999 | Hyatt | |
| 6,048,891 A | 4/2000 | Wechter | |

FOREIGN PATENT DOCUMENTS

WO    WO 00/18009    3/2000

OTHER PUBLICATIONS

Takata, Jiro; Ito, Sanae; Karube, Yoshiharu; Nagata, Yoshiko; Matsushima, Yoshikazu; Water–soluble prodrug of vitamin E for parenteral use and its effect on endotoxin–induced liver toxicity CA 126:246305 (1997).*
Hattori, Akihiro, et al., "A fluorimetric, column–switching HPLC and its application to an elimination study of LLU–α enantiomers in rat plasma", Biomedical Chromatography, Apr. 2001, pp. 95–99, vol. 15, John Wiley 7 Sons, Ltd.
Hattori, Akihiro, et al., "Production of LLU–α Following an Oral Administration of γ–Tocotrienol of γ–Tocopherol to Rats," Biol. Pharm. Bull., Nov. 2000, pp. 1395–1397, vol. 23, No. 11, Pharmaceutical Society of Japan.
Hattori, Akihiro, et al., "Occurence and Determination of a Natriuretic Hormone, 2,7, 8–Trimethyl–21(β–Carboxyethyl)–6–hydroxy Chroman, in Rat Plasma, Urine and Bile", Analytical Biochemistry, Jun. 2000, pp. 209–215, vol. 281., Academic Press.

Jiang, Qing, et al., "γ–Tocopherol and its major metabolite, in contrast to α–tocopherol, inhibit cyclooxygenase activity in macrophages and epithelial cells", Proc. National Academy of Sciences, Oct. 10, 2000, pp. 11494–11499, vol. 97, No. 21.
Wechter, William J., et al., "A new endogenous natriuretic factor: LLU–α", Proc. National Academy of Sciences, Jun. 1996, pp. 6002–6007, vol. 93.
Murray, E. David, et al., "Endogenous Natriuretic Factors 3: Isolation and Characterization of Human Natriuretic Factors LLU–α, LLUβ$_2$, and LLU–γ", Life Sciences, Oct. 1995, pp. 2145–2161, vol. 57, No. 23, Elesivier Science Inc.
Japanese Patent Office, "Patent Abstracts of Japan", Publication No.: 02–149577, Date of Publication: Jun. 8, 1990, Application No.: 63–303049, Date of Filing: Nov. 30, 1988.
Japanese Patent Office, "Patent Abstracts of Japan", Publication No.: 02–149576, Date of Publication: Jun. 8, 1990, Application No.: 63–303050, Date of Filing: Nov. 30, 1988.
Japanese Patent Office, "Patent Abstracts of Japan", Publication No.: 01–121285, Date of Publication: May 12, 1989, Application No.: 62–280475, Date of Filing: Nov. 6, 1987.
Japanese Patent Office, "Patent Abstracts of Japan", Publication No.: 01–121284, Date of Publication: May 12, 1989, Application No.: 62–280474, Date of Filing: Nov. 6, 1987.
J. Gabara, "Digitally Adjustable Resistors in CMOS for High–Performance Applications," IEEE Journal of Solid–Sate Circuits, vol. 27, No. 8, Aug. 1992, pp. 1176–1185.
R. Farad–Rad, "A 0.4–um CMOS 10–Gb/s 4–PAM Pre–Emphasis Serial Link Transmitter," IEEE Journal of Solid–State Circuits, vol. 34, No. 5, May 1999, pp. 580–585.
C. Smythe, "ISO 8802/5 token ring local–area networks," Electronics & Communication Engineering Journal, Aug. 1999, pp. 195–297.
T. Starr, "Understanding Digital Subscriber Line Technology," Chapter 7, pp. 202–205, Prentice Hall PTR, Upper Saddle River, NJ, 1999.

* cited by examiner

Primary Examiner—Amelia Owens
(74) Attorney, Agent, or Firm—Snider & Associates; Ronald R. Snider

(57) ABSTRACT

The object of the present invention is to provide a tocotrienol derivative which is highly water-soluble and shows high bioavailability in the living body and γ-CEHC delivering agent.

(I)

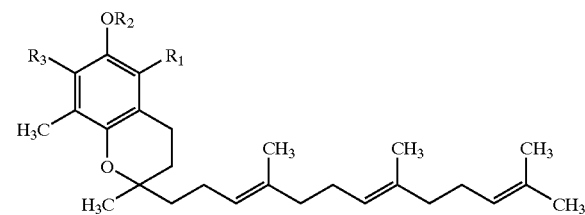

(A tocotrienolcarboxylic acid ester derivative represented by the general formula (I). (wherein $R_2$ means a carboxylic acid residue having a nitrogen substituent, and $R_1$ and $R_3$ mean a hydrogen atom or a methyl group.))

10 Claims, 13 Drawing Sheets

TOCOTRIENOL DERIVATIVE, PROCESS FOR PRODUCING THE SAME AND γ-CEHC DELIVERING AGENT

RELATED APPLICATION

The present application claims the priority of Japanese Patent Application No.2000-268885 filed on Sep. 5, 2000, which is incorporated herein.

1. Field of the Invention

The present invention relates to a tocotrienol derivative, a process for producing the same and a γ-CEHC delivering agent, in particular, an improvement in its bioavailability.

2. Background of the Invention

It was revealed that LLU-α (Loma Linda University-α) is one of natriuretic factors isolated and purified from urine of a uremic patient (Murry E. D. Jr. D., DeWind S. A., Bigornia A. E., D'Amico D. C., King J. G., Pham T., Levine B. H., Jung M. E., Wechter W J., Life Sci. 57, 2145–2161(1995)) and is the same compound as 2,7,8-trimethyl-(β-carboxyethyl)-6-hydroxychromane (γ-CEHE: the following formula) which is a γ-tocopherol metabolite (Wechter W. J., Kantoci D., Murray E. D. Jr. D'Amico D. C., Jung M. E. Wang W -H., Ptoc. Natl. Acad. Sci USA 93, 6002–6007 (1996)).

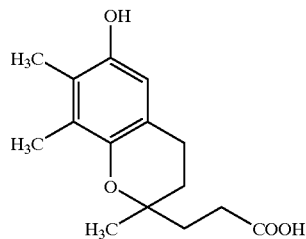

This LLU-α is considered to be a natriuretic factor because it does not affect on a sodium pump of nephron, average arterial pressure and filtration rate of glomerulus, does not inhibit an isozyme of Na+/K+-ATPase and shows the reversible inhibition only on a 70 pS potassium channel of ascending leg of Henle ansa. Therefore, LLU-α is expected as a diuretic having little side effects on cardiac muscle accompanied by potassium transfer. LLU-α has an asymmetric carbon at 2-position and there are S-LLU-α and R-LLU-α. S-LLU-α has the strongest potassium channel inhibiting activity and S-LLU-α has a R part at a 2-position and is a main metabolite of d-γ-tocopherol.

γ-CEHC was revealed to have effects of inhibiting cyclooxygenase-2 (COX-2)(Jiang Q., Elson-Schwab I., Courtemanche C., Ames B. N., Proc. Natl. Acad. Sci. USA97, 11494–11499(2000)) and is expected as an anti-inflammatory agent or an anti-cancer agent having little side effect. In addition, since γ-CEHC has the chromanol structure, it can function also as an excellent antioxidant.

On the other hand, it has been revealed that natural type d-γ-tocotrienol in which an asymmetric carbon at a 2-position of chroman is R is metabolized effectively into S-γ-CEHC in the living body of a rat (Hattori A., Fukushima T., Yoshimura H., Abe K., Imai K., Biol. Pharm Bull.,23, 1395–1397(2000)).

As described above, in order that γ-CEHC exerts the functions as a diuretic, an anti-inflammatory agent, an anti-cancer agent or an antioxidant effectively, it is essential to maintain dynamic bioavailability and quantitative bioavailability of γ-CEHC. For attaining the maintenance, a method of using γ-CEHC itself is contemplated. However, it was revealed that when racemic γ-CEHC is administered to a SD rat intravenously, a biological half-life of S-γ-CEHC in plasma is 2 minutes or shorter, that of R-γ-CEHC is about 1 hour and, in particular, S-γ-CEHC having the high activity has a very short half-life (Hattori A., Fukushima T., Hamamura K., Kato M., Imai K., Biomed. Chromatogr., in press). Therefore, it is very difficult to maintain bioavailability of γ-CEHC using γ-CEHC itself.

On the other hand, since γ-tocotrienol and γ-tocopherol are metabolized effectively into γ-CEHC in the living body, there can be contemplated a method of maintaining bioavailability of γ-CEHC by maintaining a level of γ-tocotrienol or γ-tocopherol in the living body. A method of performing drug delivery of LLU-α (γ-CEHC) using γ-tocopherol is described in U.S. Pat. No. 6,048,891. However, both γ-tocotrienol and γ-tocopherol are unsteable to oxidation and are a compound which is an oily substance having the high viscosity and is not dissolved to water at all, these physicochemical properties make them impossible to be administered by injection. In addition, it is difficult to handle them from a viewpoint of manufacturing pharmacy and there is a problem on storage stability. For these reasons, a method of solubilizing them by adding a large amount of a nonionic surfactant has been studied in order to prepare an aqueous preparation or aqueous cosmetic of tocotrienol. However, a large amount of an surfactant may cause a severe problem such as anaphylaxis shock and the like. In addition, as a tocotrienol derivative having water dispersion or water solubility, tocotrienolsuccinic acid ester and polyethylene glycol derivative of tocotrienolsuccinic acid ester are known (U.S. Pat. No. 5,869,704). However, there is still left a problem that these compounds are oily or waxy at room temperature and reconversion into tocotrienol in the living body is very slow. Therefore, it is difficult to maintain bioavailability of γ-tocotrienol and γ-tocopherol and, consequently, it is also difficult to maintain bioavailability of γ-CEHC.

Like this, the natures normally harbored by tocopherol and tocotrienol have many disadvantageous points in order to enhance their bioavailability.

SUMMARY OF THE INVENTION

The first object of the present invention is to provide a tocotrienol derivative which is highly water-soluble and can produce free tocotrienol in the living body.

The second object of the present invention is to provide a γ-CEHC delivering agent containing a 6-chromanolcarboxylic acid ester derivative which can produce γ-CEHC in the living body.

That is, present tocotrienolcarboxylic acid ester derivative is characterized in that it is represented by the general formula (I):

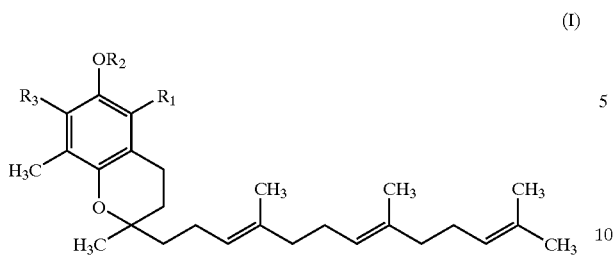

(I)

(wherein $R_2$ means a carboxylic acid residue having a nitrogen substituent, and $R_1$ and $R_3$ mean a hydrogen atom or a methyl group.)

In addition, in the present invention, it is suitable that the carboxylic acid residue having a nitrogen substituent is at least one selected from the group consisting of residues of amino acid, N-acylamino acid, N-alkylamino acid, N,N-dialkylamino acid, pyridinecarboxylic acid and hydrogen halide salt or alkylsulfonic acid salt thereof.

In addition, a process for producing the tocotrienolcarboxylic acid ester derivative of the present invention comprises protecting a primary or secondary amino group or an amino group of an amino acid having a hydroxy group or a thiol group on a side chain with a protecting group, and subjecting the protecting group-coupled amino acid and tocotrienol to an esterifying reaction.

In addition, the other process for production of the present invention comprises performing an esterifying reaction of a hydrogen halide salt of N,N-dialkylamino acid and tocotrienol in the presence of an active esterifying reagent.

Since a tocotrienol derivative represented by the general formula (I) has an asymmetric carbon at a 2-position of a chromanol skeleton, steric isomers such as d isomer and dl isomer exist The present invention includes these isomers.

In addition, a γ-CEHC delivering agent of the present invention includes a water-soluble 6-chromanol derivative represented by the general formula (II) and releases 2,7,8-trimethyl-(β-carboxyethyl)-6-hydroxychromane (γ-CEHC) in the living body. (II):

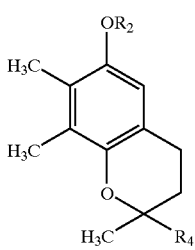

(II)

(wherein $R_2$ means a carboxylic acid residue having a nitrogen substituent.)

In addition, an agent for oral administration of the present invention contains a water—soluble 6—chromanolcarboxylic acid ester derivative represented by general formula (III):

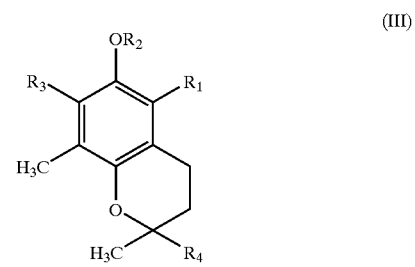

(III)

(wherein $R_2$ means a carboxylic acid residue having a nitrogen substituent, and $R_1$ and $R_3$ mean a hydrogen atom or a methyl group.) In the above general formulas II and III, $R_4$ is a residue represented by the following formula:

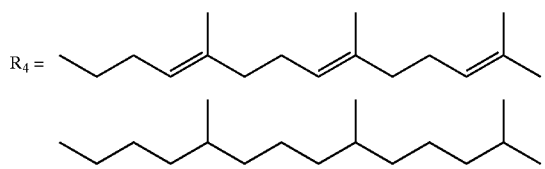

In addition, a method of improving bioavailability of γ-CEHC of the present invention comprises administering the compound of the general formula (II) to the living body.

DETAILED DESCRIPTION OF THE PREFERRED EMBODIMENT

Figure 1:
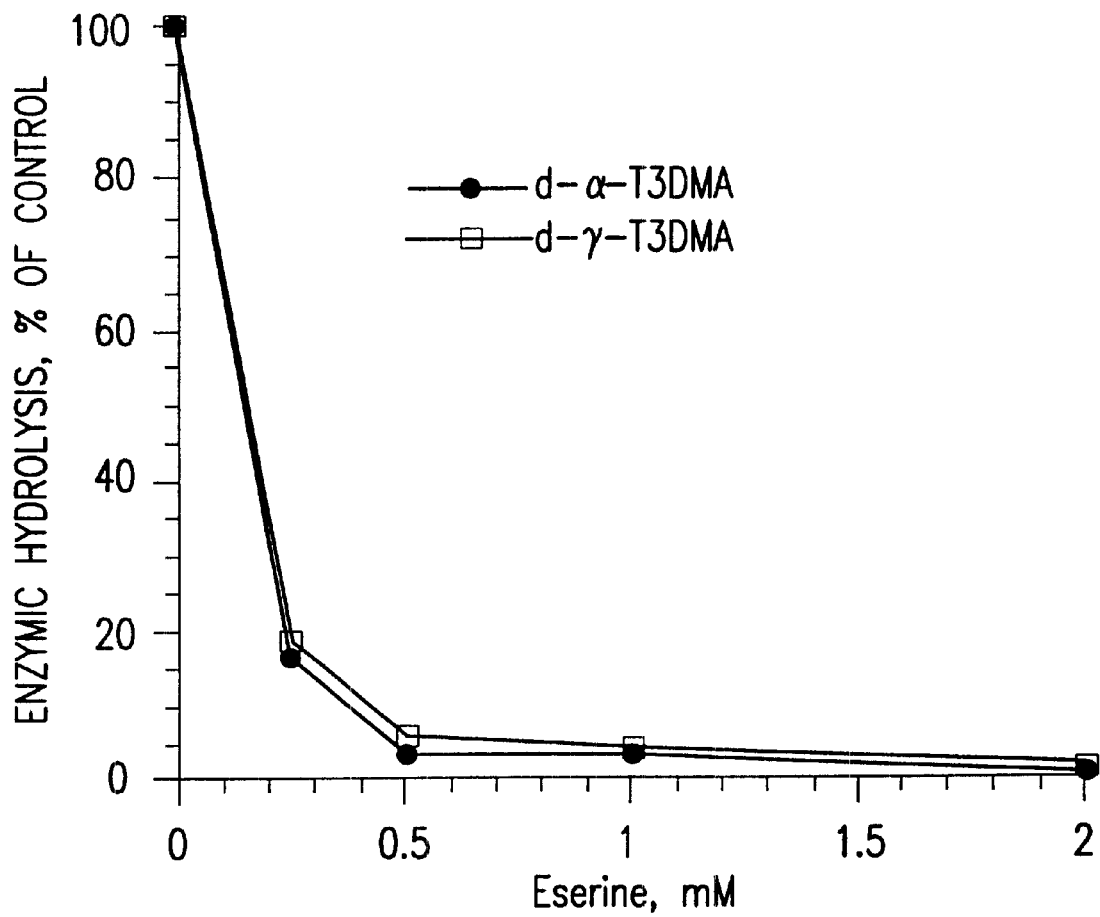
FIG. 1 is a view for explaining the effect of an esterase inhibiting agent on an reaction of hydrolyzing a tocotrienol carboxylic acid ester derivative.
Figure 2A:
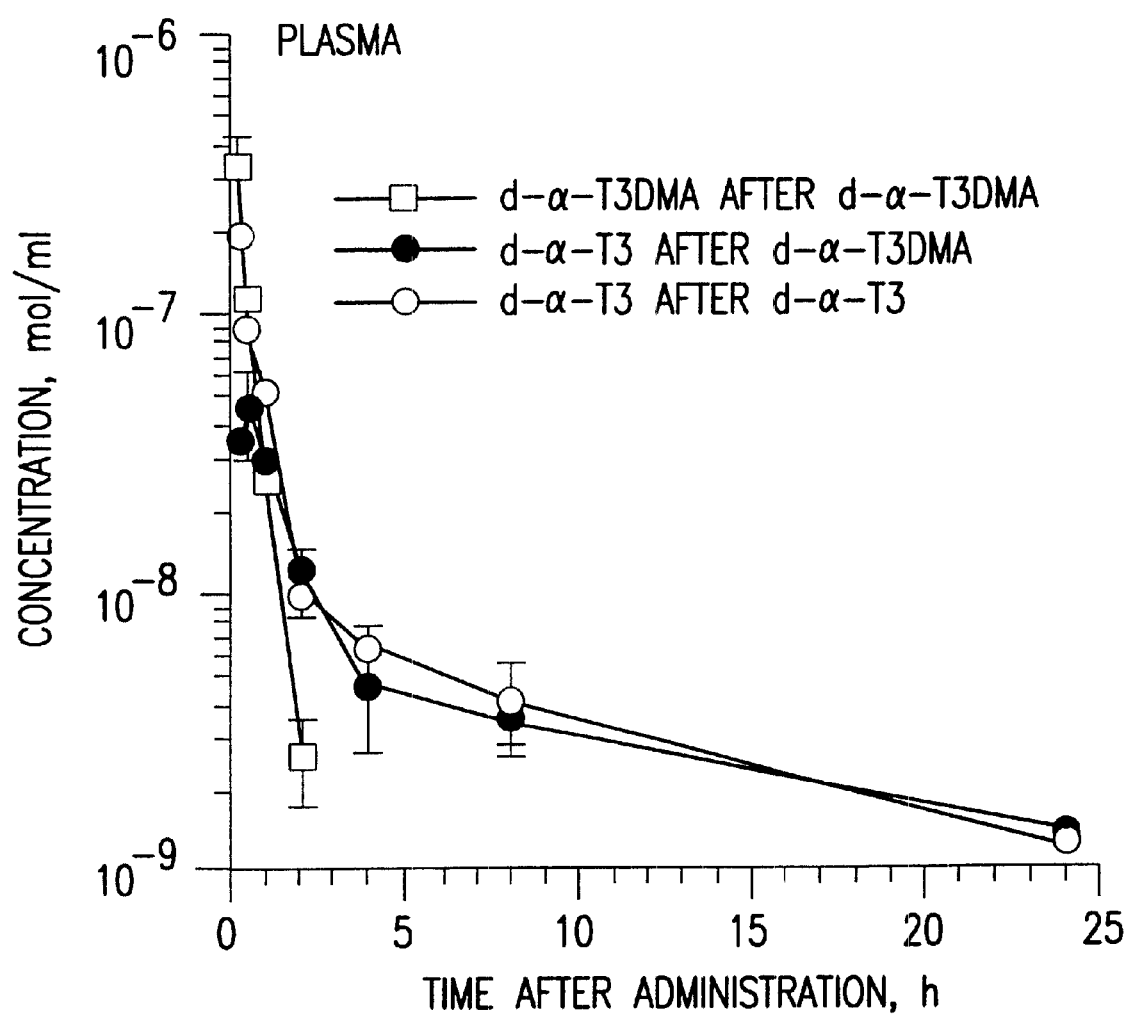
FIG. 2 is a view for explaining the results of study on kinetics in the living body of a rat when d-α-T3DMA and d-α-T3 are administered.
Figure 2B:
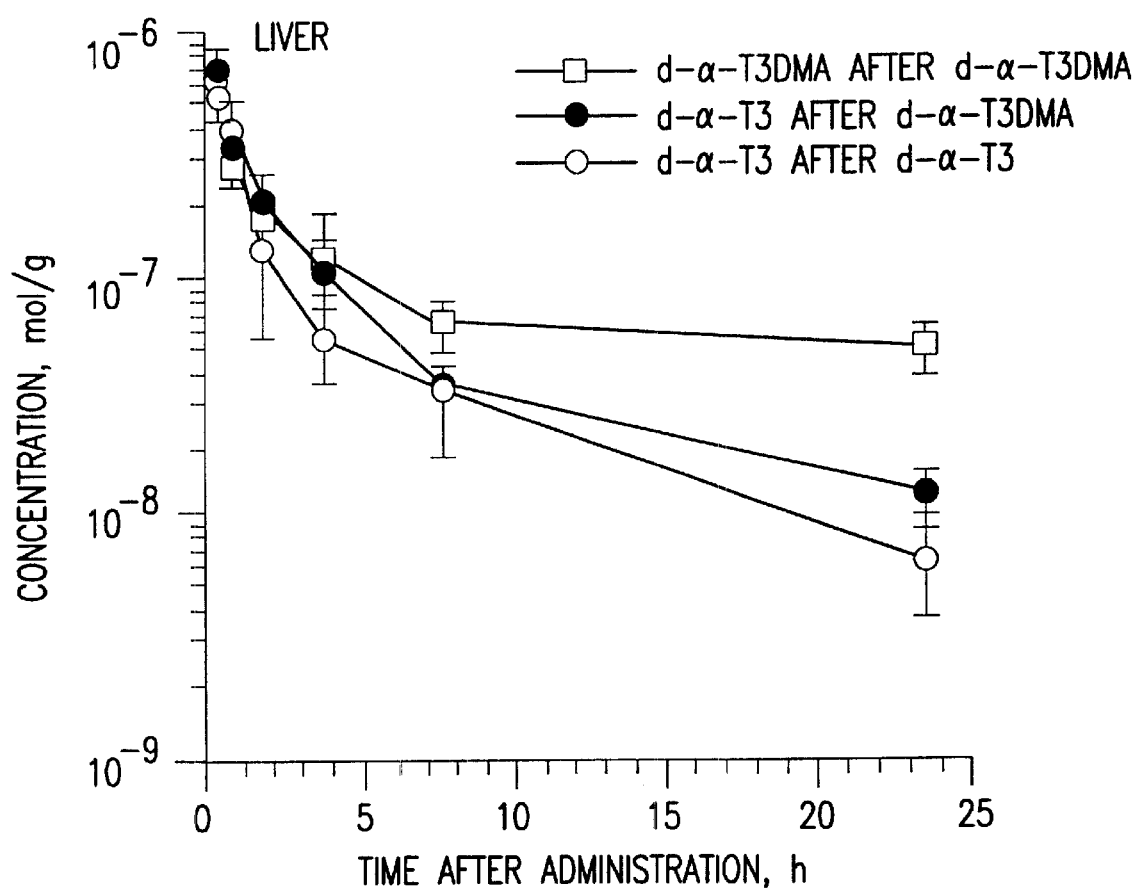
Figure 2C:
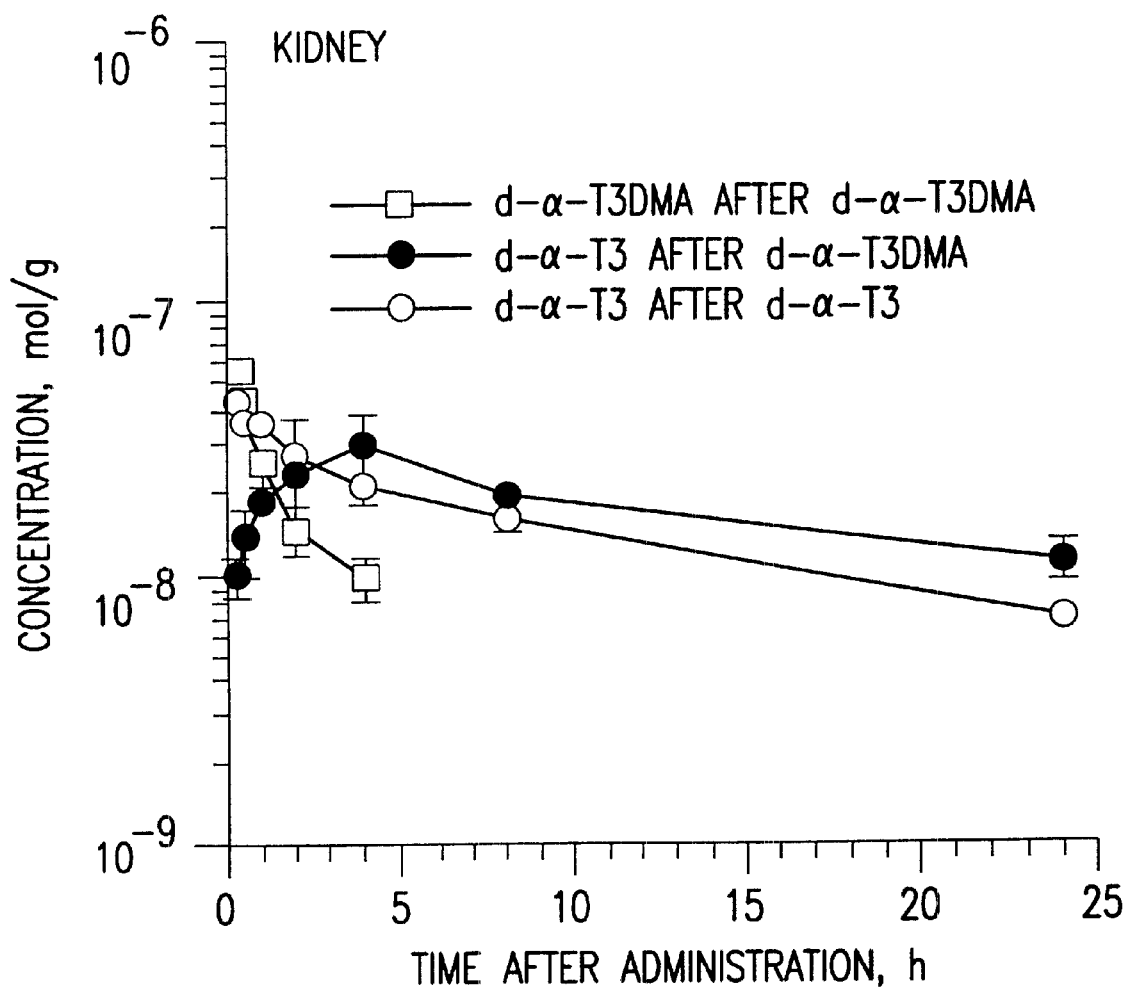
Figure 2D:
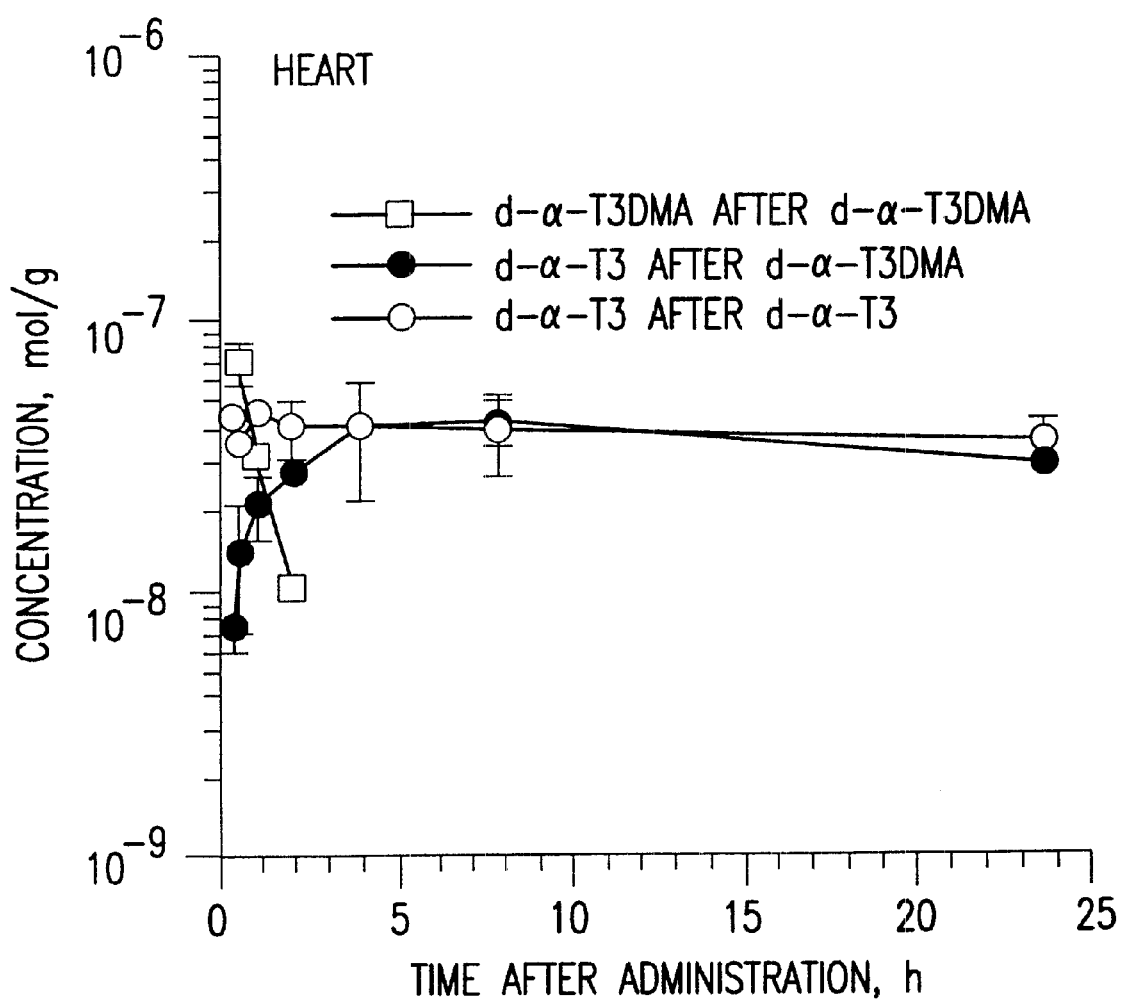
Figure 3A:
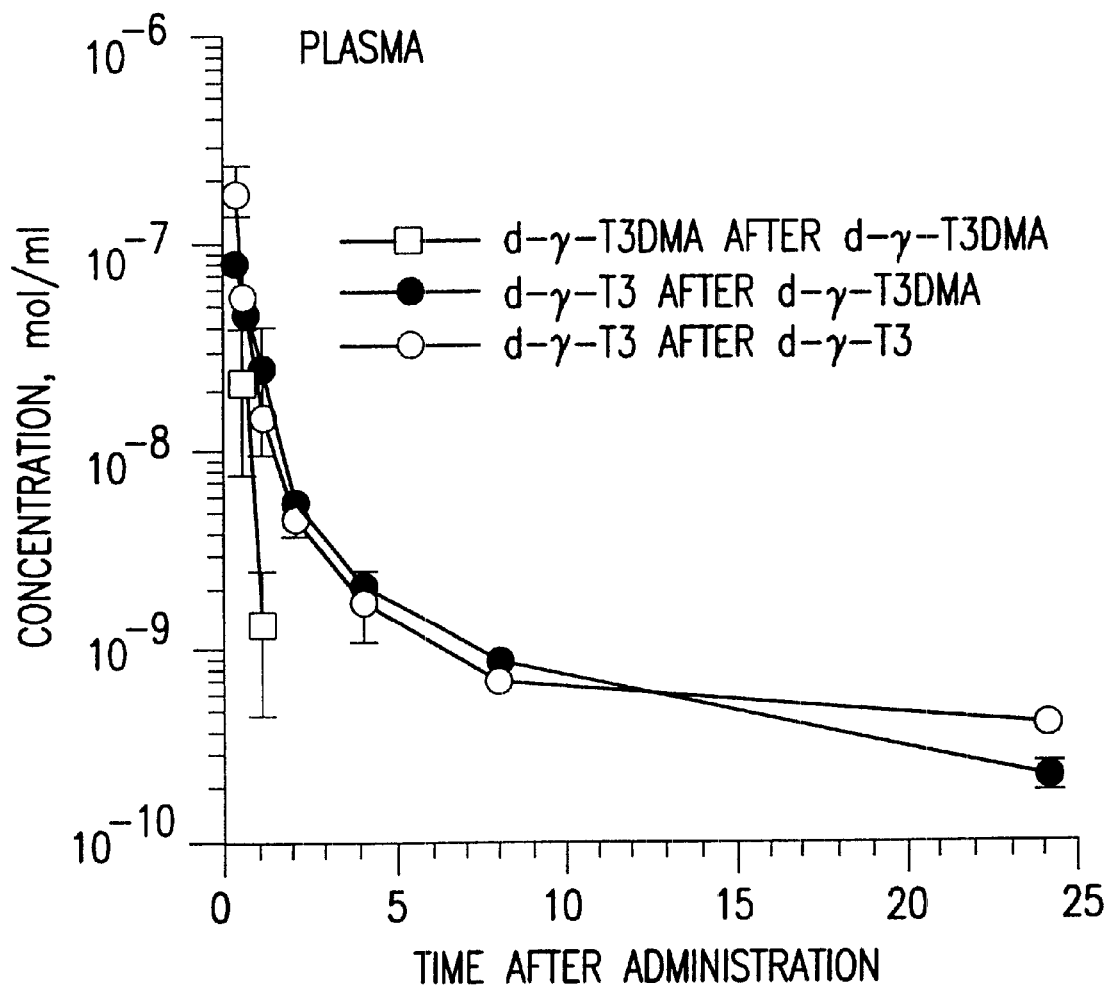
FIG. 3 is a view for explaining the results of study on kinetics in the living body of a rat when d-γ-T3DMA and d-γ-T3 are administered.
Figure 3B:
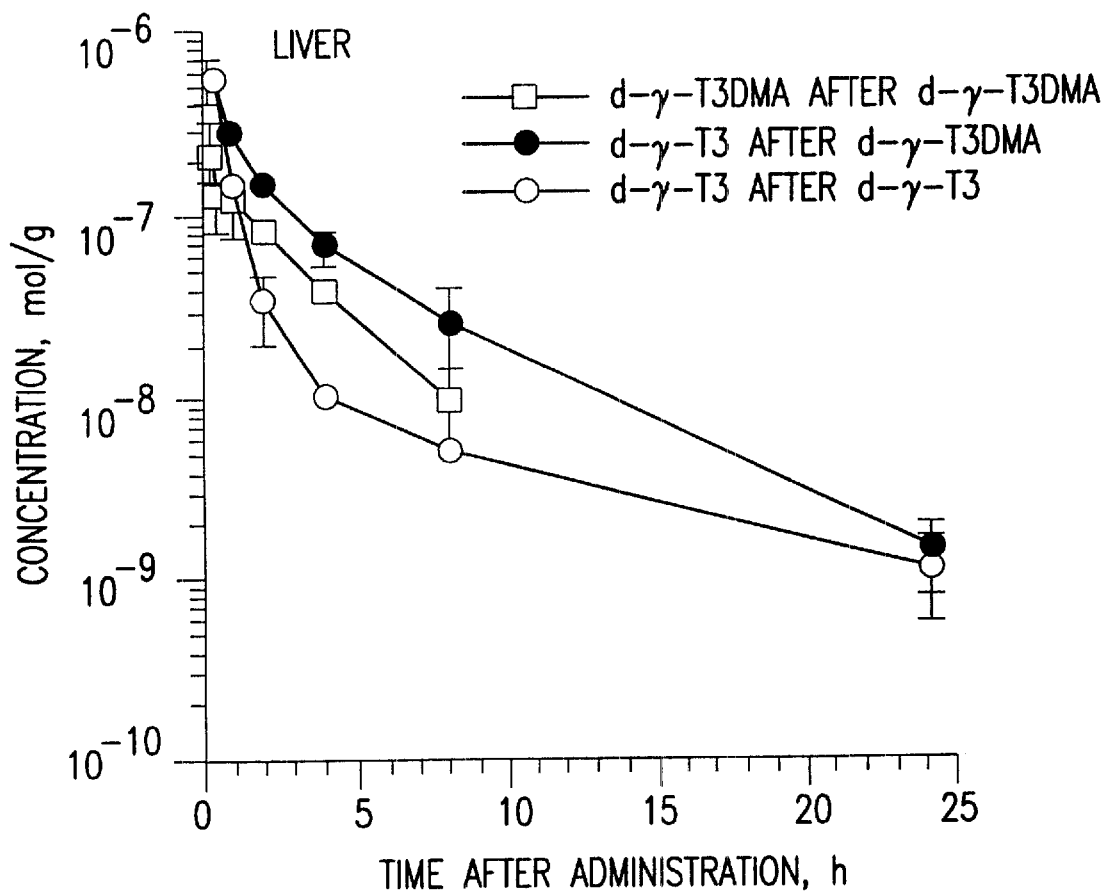
Figure 3C:
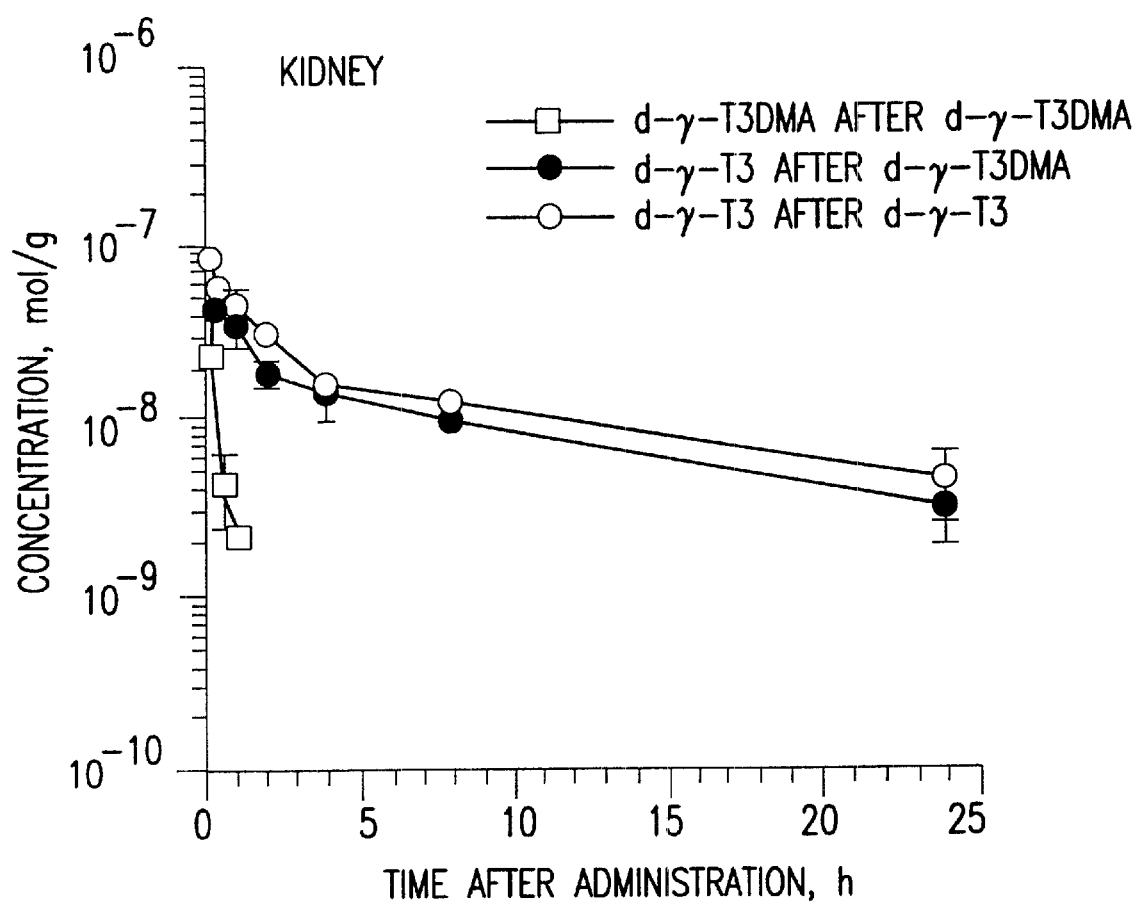
Figure 3D:
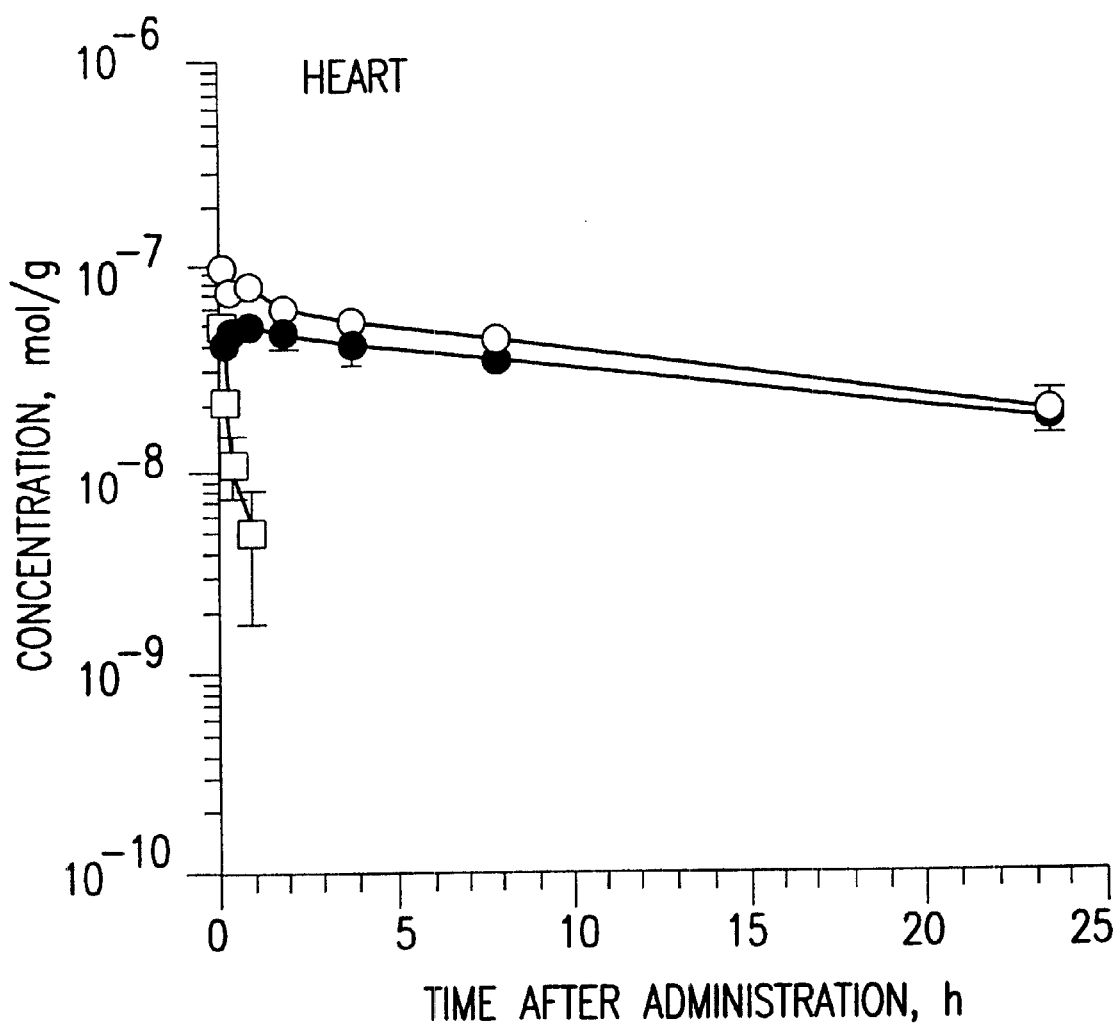

Preferable embodiments of the present invention will be explained below.

In the present invention, carboxylic acid residues having a nitrogen substituent are preferable in which a hydrogen atom or 1 or 2 alkyl groups or acyl groups are binded to a nitrogen atom. As this alkyl group, there can be exemplified straight or branched alkyl groups having a carbon number of 1 to 6 such as methyl group, ethyl group, n-propyl group, n-butyl group, n-pentyl group, n-hexyl group, isopropyl group, isobutyl group, 1-methylpropyl group, tert-butyl group, 1-ethylpropyl and isoamyl group. In particular, methyl group and ethyl group are preferable. In addition, a hydrocarbon chain when it has an acyl group can be defined similarly.

An amino group and a carbonyl group are binded preferably with a straight, branched or cyclic alkylene group having a carbon number of 1 to 7. The branched alkylene group means, for example, alkylene groups derived from a alkyl group such as isopropyl, isobutyl, tert-butyl and 1-ethylpropyl. The cyclic alkylene group means alkylene groups including a cyclopentane ring, a cyclohexane ring or a methylcyclohexane ring in the structure. Particularly preferable alkylene group is methylene group or ethylene group.

As the hydrogen halide salt, HCl salt and HBr salt are preferable. In the present invention, hydrogen halide salt is crystallized or solidified in many cases and there is an advantage that handling upon formulation into preparations becomes easy.

In addition, an example of the alkylsulfonic acid salt includes methanesulfonic acid. In the case of this alkylsulfonic acid salt, low hygroscopic solidification is possible.

Next, as a process for producing a tocotrienol derivative of the present

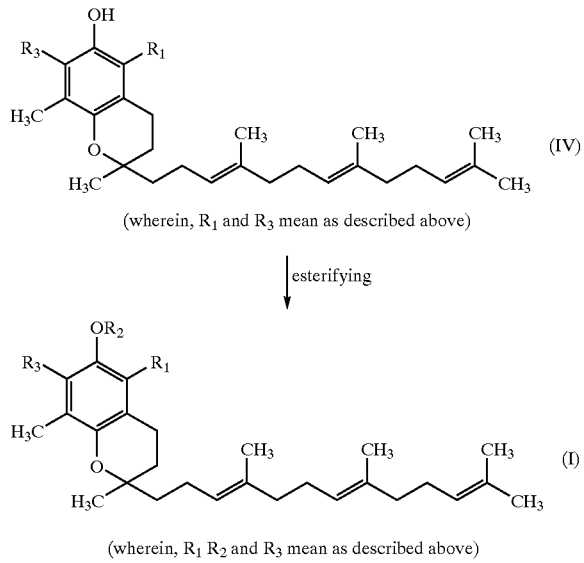

(wherein, $R_1$ and $R_3$ mean as described above)

esterifying (wherein, $R_1$ $R_2$ and $R_3$ mean as described above)

invention, there can be exemplified as follows:

An end substance (I) of the present invention can be obtained by normally esterification-reacting tocotrienols represented by the general formula (IV) with a carboxylic acid having a nitrogen substituent or a reactive derivative thereof or hydrogen halide salt thereof by the conventional method.

The reaction for esterifying tocotrienols is according to the conventional reaction When a primary or secondary amino group or an amino acid having a hydroxy group or a thiol group on a side chain is esterified, it is preferable that those groups are used after protected with a suitable protecting group such as tert-butoxycarbonyl group (hereinafter referred to as t-BOC group) and benzyloxycarbonyl group (hereinafter referred to as Z group).

In addition, N,N-dialkylamino acid is preferably reacted using a hydrogen halide salt in the presence of an active esterifying reagent such as dicyclohexylcarbodiimide (hereinafter referred to as DCC) and N,N-disuccinimidooxalate (hereinafter referred to as DSO). As a solvent upon this, anhydrous pyridine is preferable.

In addition, among methods using a reactive acid derivative, a method using acid halogenite, particularly acid chloride is preferable. As a solvent upon this, a mixture of anhydrous benzene-anhydrous pyridine is preferable. A hydrogen halide salt and an alkylsulfonic acid salt are prepared by reacting a free amino acid ester with hydrogen halide or alkylsulfonic acid by the conventional method. In addition, a hydrogen halide salt can be prepared by preparing N-acylamino acid ester which is thereafter deprotected with hydrogen halide by the conventional method.

A tocotrienolcarboxylic acid ester derivative can be a bile acid salt.

Here, more specifically, the bile acid salt refers to salts of taurocholic acid, glycocholic acid, cholic acid, taurodeoxycholic acid, deoxycholic acid, taurochenodeoxycholic acid, glycochenocholic acid, ursodeoxycholic acid and the like. And, by reacting the aforementioned tocotrienol carboxylic acid ester with these bile acids, a bile acid salt can be obtained. A bile acid salt of a tocotrienol carboxylic acid ester can be obtained, for example, by reacting using a solvent of a lower alcohol such as methanol, ethanol and propanol and, after completion of the reaction, distilling the solvent off under reduced pressure.

An end substance (I) obtained by the present invention is easily hydrolyzed by a hydrolase which is ubiquitously present in the living body to produce tocotrienol. A hydrogen halide salt and an alkylsulfonic acid salt are a crystalline powder, are easy and simple in handling from a viewpoint of manufacturing pharmacy, and have comparatively high water-solubility. Therefore, they are useful as preparations which can be administered intravenously, eyedrops, oral agents and aqueous paints.

Examples of water-soluble 6-chromanolcarboxylic acid ester derivatives which produce tocopherol in the living body in the present invention include derivatives disclosed in JP-A 2-149576, JP-A 2-149577, JP-A 1-121284 or JP-A 1-121285. However, in these references, maintenance of bioavailability of γ-CEHC and effectiveness at oral administration are not studied at all.

Examples of tocotrienolcarboxylic acid ester derivatives which are particularly suitable in the present invention will be explained below. The present invention is not limited to these Examples.

EXAMPLES 1–18

Tocotrienol derivatives shown in Table 1 and Table 3 were prepared by the methods shown in the following Preparation Methods A–D. In addition, 1H-NMR spectra of the compounds shown in Table 1 are shown in Table 2.

Preparation Method A 0.1 mol of amino acid is dissolved in 100 ml of distilled water-dioxane (1:1, v/v), 30 ml of triethylamine is added and, further, di-tert-butyl dicarbonate is gradually added, which is stirred at room temperature for 30 minutes. Dioxane is distilled off under reduced pressure, 50 ml of an aqueous sodium bicarbonate solution (0.5 M) is added and the mixture is washed with 100 ml of ethyl acetate. The ethyl acetate layer is washed with 50 ml of a sodium bicarbonate solution, the aqueous layer is combined therewith, an aqueous citric acid solution (0.5 M) is added under ice-cooling to acidic (pH3), sodium chloride is saturated, which is thereafter extracted with ethyl acetate (100 ml×3 times). After the extract is dehydrated with anhydrous sodium sulfate, the solvent is distilled off under reduced pressure, the oily residue is crystallized by adding isopropyl ether or cooling, to obtain N-t-BOC amino acid.

5 mmol of tocotrienol, 5 mmol of N-t-BOC amino acid and 5 mmol of DCC are added to 30 ml of anhydrous pyridine under argon gas atmosphere and the mixture is stirred for 20 hours. The solvent is distilled off under reduced pressure, ethyl acetate is added to the residue and the soluble fraction is extracted (100 ml×2 times). The extract is concentrated under reduced pressure, and the residue is separated and purified with silica gel column chromatography (eluting solvent; n-hexane-ethyl acetate= 9:1) to obtain tocotrienol N-t-BOC-amino acid ester.

Tocotrienol N-t-BOC-amino acid ester is dissolved in a small amount of acetone, hydrochloric acid-dioxane (2.5–4.0 N) is added so that an amount of hydrochloric acid is an amount corresponding to 20-fold mole amount of the ester, the mixture is stirred for 1 hour, and the solvent is distilled off under reduced pressure. The residue is recrystallized with acetone-methanol or ethyl acetate-methanol to obtain hydrochloride of tocotrienolamino acid.

Preparation Method B 3 mmol of hydrochloride of tocotrienolamino acid is added to 150 ml of water, sodium bicarbonate is added to adjust pH of the solution to 7–8, and the solution is extracted with ethyl acetate (100 ml×3 times). After the extract is dehydrated with anhydrous sodium sulfate, the solvent is distilled off under reduced pressure to obtain oily tocotrienolamino acid.

Preparation Method C 5 mmol of tocotrienol, 5 mmol of N,N-dialkylamino acid chloride and 5 mmol of DCC are added to 30 ml of anhydrous pyridine and the mixture is stirred at room temperature for 20 hours under argon gas atmosphere. The solvent is distilled off under reduced pressure, the residue is suspended in distilled water, sodium bicarbonate is added to adjust pH of the solution to 7–8, the solution is extracted with ethyl acetate (100 ml×3 times). After the extract is dehydrated with anhydrous sodium sulfate, the solvent is distilled off under reduced pressure, and the residue is separated and purified by silica gel column chromatography (eluting solvent: n-hexane-ethyl acetate=8:2) to obtain tocotrienol N,N-dialkylamino acid.

Preparation Method D 2 mmol of tocotrienolamino acid or tocotrienol N,N-dialkylamino acid is dissolved in 20 ml of acetone, hydrochloric acid-dioxane (2.5–4.0 N) (an amount of hydrochloric acid corresponds to 10-fold mole amount of the ester) or 2 mmol of alkylsulfonic acid is added, and the solvent is distilled off under reduced pressure. The residue is recrystallized with acetone-methanol or ethyl acetate-methanol system to obtain hydrochloride of tocotrienolamino acid or tocotrienol N,N-dialkyl amino acid.

The specific chemical formulas of the compounds of the present invention and their physical properties as well as a process for producing them are shown in Tables 1 and 3. Regarding Examples 1–7, mass spectroscopy (m/z, FAB-MS) and nuclear magnetic resonance spectra (1 H-NMR, δ ppm, internal standard TMS) are shown in Table 2.

TABLE 1

| example No | compound | R1 | R2 | R3 | salt | configuration | melting point | preparation method |
|---|---|---|---|---|---|---|---|---|
| 1 | d-α-tocotrienyl aminoacetate hydrochloride | $CH_3$ | $NH_2CH_2CO-$ | $CH_3$ | HCl | white crystal | 167–173 | A,D |
| 2 | d-α-tocotrienyl N-methylaminoacetate hydrochloride | $CH_3$ | $CH_3NHCH_2CO-$ | $CH_3$ | HCl | white crystal | 170–173 | A,D |
| 3 | d-γ-tocotrienyl aminoacetate hydrochloride | H | $NH_2CH_2CO-$ | $CH_3$ | HCl | white crystal | 195–198 | A,D |
| 4 | d-γ-tocotrienyl N-methylaminoacetate hydrochloride | H | $CH_3NHCH_2CO-$ | $CH_3$ | HCl | white crystal | 130–132 | A,D |
| 5 | d-α-tocotrienyl N,N-dimethylaminoacetate hydrochloride | $CH_3$ | $(CH_3)_2NCH_2CO-$ | $CH_3$ | HCl | white crystal | 186–188 | B,D |
| 6 | d-γ-tocotrienyl N,N-dimethylaminoacetate hydrochloride | H | $(CH_3)_2NCH_2CO-$ | $CH_3$ | HCl | white crystal | 160–161 | B,D |
| 7 | d-δ-tocotrienyl N,N-dimethylaminoacetate hydrochloride | H | $(CH_3)_2NCH_2CO-$ | H | HCl | white solid | Unmeasurable (because of its absorbing nature) | A,D |

TABLE 2

| example | mass spectrum | $^1$H-NMR spectrum |
|---|---|---|
| 1 | 482(M − HCl + H$^+$) | (in CDCl$_3$) 8.76(2H, s), 509(3H, m), 4.09(2H, s), 2.50(2H, t), 2.11 − 1.89(19H, m, including 2.02(3H, s), 1.92(3H, s), 1.89(3H, s)), 1.74 − 1.47(16H, m, including 1.67(3H, s), 1.59(6H, s), 1.55(3H, s)), 127(3H, s) |
| 2 | 496(M − HCl + H$^+$) | (in CDCl$_3$) 9.95(1H, s), 5.10(3H, m), 4.09(2H, s), 2.80(3H, s), 2.56(2H, t), 2.12 − 1.97(19H, m, including 2.07(3H, s), 200(3H, s), 1.97(3H, s)), 1.78 − 1.52(16H, m, including 1.67(3H, s), 1.59(6H, s), 1.56(3H, s)), 1.27(3H, s) |
| 3 | 468(M − HCl + H$^+$) | (in. CDCl$_3$) 8.67(2H, s), 6.61(1H, s), 5.10(3H, m), 4.04(2H, s), 2.60(2H, m), 2.16 − 1.92(16H, m, including 2.02(3H, s), 1.92(3H, s)), 1.69 − 1.49(16H, m, including 1.67(3H, s), 1.58(6H, s), 1.55(3H, s)), 1.24(3H, s) |

TABLE 2-continued

| example | mass spectrum | $^1$H-NMR spectrum |
|---|---|---|
| 4 | 482(M − HCl + H$^+$) | (in CDCl$_3$) 10.01(1H, s), 6.66(1H, s), 5.11(3H, m), 4.04(2H, s), 281(3H, s), 2.66(2H, m), 2.10 − 1.95(16H, m, including 2.08(3H, s), 2.01(3H, s)), 1.69 − 1.49(16H, m, including 1.67(3H, s), 1.59(6H, s), 1.56(3H, s)), 1.24(3H, s) |
| 5 | 510(M − HCl + H$^+$) | (in CDCl$_3$) 5.10(3H, m), 4.60(2H, s), 3.06(6H, s), 2.64(2H, t), 2.15 − 1.93(19H, m, including 2.11(3H, s), 2.04(3H, s), 2.01(3H, s)), 1.85 − 1.54(16H, m, including 1.65(3H, s), 1.58(3H, s), 1.56(3H, s)), 1.27(3H, s) |
| 6 | 496(M − HCl + H$^+$) | (in CDCl$_3$) 6.63(1H, s), 5.10(3H, m), 4.21(2H, s), 3.09(6H, s), 2.72(2H, m), 2.13 − 1.95(16H, m, including 2.12(3H, s), 2.02(3H, s)), 1.81 − 159(16H, m, including 168(3H, s), 1.60(6H, s), 1.59(3H, s)), 1.28(3H, s) |
| 7 | 482(M − HCl + H$^+$) | (in CDCl$_3$) 6.73(1H, s), 6.69(1H, s), 5.12(3H, m), 4.15(2H, s), 3.08(6H, s), 2.74(2H, m), 2.16 − 1.90(13H, m, including 2.16(3H, s)), 1.86 − 1.52(16H, m, including 1.67(3H, s), 1.60(6H, s), 156(3H, s)), 1.28(3H, s) |

Generally, tocotrienols are very viscous and highly oily substance, handling including accurate weighing is difficult. To the contrary, hydrogen halides of tocotrienolcarboxylic acid ester derivatives of the present invention become crystal or solid as shown in the above Examples 1 to 7 and, thus, they have the advantage that handling becomes extremely simple. In this respect, the aforementioned previous tocotrienolsuccinic acid esters or the like are oily or waxy and handling is difficult like general tocotrienols. And, it is mentioned specially that hydrogen halide is a particularly preferable form in the present invention.

Water-solubility Test

1) Test Procedures

Each 0.250 mmol of d-α-tocotrienol, d-γ-tocotrienol, d-δ-tocotrienol, d-α-tocotrienol aminoacetate hydrochloride (Example 1: hereinafter, d-α-T3AA), d-α-tocotrienol N-methylaminoacetate hydrochloride (Example 2:hereinafter, d-α-T3MA), d-α-tocotrienol N,N-dimethylaminoacetate hydrochloride (Example 5: hereinafter, d-α-T3DMA), d-γ-tocotrienol aminoacetate hydrochloride (Example 3:hereinafter, d-γ-T3AA), d-γ-tocotrienol N-methylaminoacetate hydrochloride (Example 4:hereinafter, d-γ-T3MA), d-γ-tocotrienol N,N-dimethylaminoacetate hydrochloride (Example 6:hereinafter, d-γ-T3DMA), or d-δ-tocotrienol N,N-dimethylaminoacetate hydrochloride (Example 7:hereinafter d-δ-T3DMA) was taken in a volumetric flask, distilled water was added to 5 ml, the solution was stirred at 20° C. for 24 hours, the concentration of each added compound in the solution was measured by high performance liquid chromatography (HPLC).

2) Results

All of d-α-tocotrienol, d-γ-tocotrienol and d-δ-tocotrienol were below detection limit of HPLC and the solubilities could not measured. All of d-α-T3AA, d-α-T3MA, d-γ-T3AA, d-γ-T3MA, d-γ-T3DMA and d-δ-T3DMA became a solution, and the solubilities were above 50 mM.

Hydrolyzability Test

1) Procedures d-α-tocotrienol N,N-dimethylaminoacetate hydrochloride (Example 5:hereinafter, d-α-T3DMA), d-α-tocotrienol N-methylaminoacetate hydrochloride (Example 2:hereinafter, d-α-T3MA), d-γ-tocotrienol N,N-dimethylaminoacetate hydrochloride (Example 6:hereinafter, d-γ-T3DMA), d-γ-tocotrienol N-methylaminoacetate hydrochloride (Example 4:hereinafter, d-γ-T3MA), or d-γ-tocotrienolaminoacetate hydrochloride (Example 3:hereinafter, d-γ-T3AA) were added to a solution of SD rat liver microsome and rat plasma

TABLE 3

| example No. | compound | R1 | R2 | R3 | state | mass spectrum | preparation method |
|---|---|---|---|---|---|---|---|
| 8 | d-α-tocotrienyl N-t-BOC-aminoacetate | CH$_3$ | N-t-BOC-NHCH$_2$CO— | CH$_3$ | oily | 582 | A |
| 9 | d-α-tocotrienyl N-t-BOC-N-methylaminoacetate | CH$_3$ | N-t-BOC-N(CH$_3$)CH$_2$CO— | CH$_3$ | oily | 596 | A |
| 10 | d-γ-tocotrienyl N-t-BOC-aminoacetate | H | N-t-BOC-NHCH$_2$CO— | CH$_3$ | oily | 568 | A |
| 11 | d-γ-tocotrienyl N-t-BOC-N-methylaminoacetate | H | N-t-BOC-N(CH$_3$)CH$_2$CO— | CH$_3$ | oily | 582 | A |
| 12 | d-α-tocotrienyl aminoacetate | CH$_3$ | NH$_2$CH$_2$CO— | CH$_3$ | oily | 482 | C |
| 13 | d-α-tocotrienyl N-methylaminoacetate | CH$_3$ | CH$_3$NHCH$_2$CO— | CH$_3$ | oily | 496 | C |
| 14 | d-γ-tocotrienyl aminoacetate | H | NH$_2$CH$_2$CO— | CH$_3$ | oily | 468 | C |
| 15 | d-γ-tocotrienyl N-methylaminoacetate | H | CH$_3$NHCH$_2$CO— | CH$_3$ | oily | 482 | C |
| 16 | d-α-tocotrienyl N,N-dimethylaminoacetate | CH$_3$ | (CH$_3$)$_2$NCH$_2$CO— | CH$_3$ | oily | 510 | C |
| 17 | d-γ-tocotrienyl N,N-dimethylaminoacetate | H | (CH$_3$)$_2$NCH$_2$CO— | CH$_3$ | oily | 496 | C |
| 18 | d-δ-tocotrienyl N,N-dimethylaminoacetate | H | (CH$_3$)$_2$NCH$_2$CO— | H | oily | 482 | C | in an isotonic phosphate buffer, and d-α-tocotrienol and d-γ-tocotrienol produced in the reaction solution at 37° C. with time were measured by high performance liquid chromatography (HPLC).

As Comparative Example, a hydrolysis test was performed on d-α-tocotrienolsuccinic acid ester (hereinafter, d-α-T3S) and d-γ-tocotrienolsuccinic acid ester (hereinafter, d-γ-T3S) similarly.

HPLC conditions: Column was CAPCELL PAK UG120, a mobile phase was methanol-acetonitrile (5:5 v/v), a rate was 0.7 ml/min, and detection was carried out by absorbance of 283 nm and fluorescent intensity (excitation 298 nm, fluorescent 325 nm).

2) Results

Dynamic parameters of production of d-α-tocotrienol and d-γ-tocotrienol in a solution of rat liver microsome and rat plasma according to Micaelis-Menten model are shown in Tables 4 and 5.

TABLE 4

| liver microsome | $Km(\times 10^{-3}$ M) | $Vmax(\times 10^{-6}$ M/min) | $Vmax/Km(\times 10^{-3}$ $min^{-1})$ |
|---|---|---|---|
| d-α-T3DMA | 5.966 | 146.5 | 24.55 |
| d-α-T3MA | 0.1091 | 1.878 | 11.11 |
| d-α-T3S | 0.03027 | 0.05588 | 1.846 |
| d-γ-T3DMA | 5.575 | 323.0 | 56.10 |
| d-γ-T3MA | 2.097 | 120.4 | 57.42 |
| d-γ-T3AA | 1.563 | 77.16 | 49.38 |
| d-γ-T3S | 0.02207 | 0.7161 | 32.44 |

TABLE 5

| plasma | $Km(\times 10^{-3}$ M) | $Vmax(\times 10^{-6}$ M/min) | $Vmax/Km(\times 10^{-3}$ min-1) |
|---|---|---|---|
| d-α-T3DMA | 0.7930 | 0.09187 | 0.1159 |
| d-α-T3MA | 1.549 | 0.5808 | 0.3749 |
| d-α-T3S | 0.5065 | 0.04946 | 0.09767 |
| d-γ-T3DMA | 0.7860 | 7.592 | 9.659 |
| d-γ-T3MA | 12.71 | 51.78 | 4.074 |
| d-γ-T3AA | 5.507 | 35.94 | 6.527 |
| d-γ-T3S | 1.052 | 1.945 | 1.849 |

Carboxylic acid esters having a nitrogen substituent of tocotrienol produced tocotrienol more rapidly as compared with tocotrienolsuccinic acid ester. Since this hydrolysis reaction is strongly inhibited by an esterase inhibitor (See FIG. 1), it was revealed that the reaction is catalyzed by an esterase. It is understood that the present compounds are an excellent derivative of tocotrienol in comparison with the previous succinic acid ester.

Animal Test

Test Example 1

1) SD male rats (weighing 260–285 g) were used while a diet was changed to crystal sugar from 16 hours before drug administration. d-α-T3DMA (Example 5), d-γ-T3DMA (Example 6), d-α-tocotrienol (hereinafter, d-α-T3), or d-γ-tocotrienol (hereinafter, d-γ-T3) was administered into left femoral vein under slight ether anesthesia. A solution of d-α-T3DMA or d-γ-T3DMA to be administered was used by dissolving it in distilled water containing 10% propylene glycol, and filtering with membrane filter (0.22 μm). A solution of d-α-T3 and d-γ-T3 to be administered was used by dissolving it using a nonionic surfactant HCO-60. Administration amounts were set to be tocotrienol equivalent 25 mg/kg, respectively. 0.25, 0.5, 1, 2, 4, 8 and 24 hours after administration, blood was taken under ether anesthesia, and liver, heart and kidney were taken. Plasma was rapidly separated and taken. A 1.15% potassium chloride solution was added at a 3-fold amount of each organ weight was added thereto, which was homogenated. 0.7 ml of ethanol was added to 0.2 ml of each sample, the mixture was stirred for 2 minutes, centrifuged, and the supernatant was analyzed by the aforementioned HPLC.

Results are shown in FIGS. 2 and 3.

FIG. 2 shows the results of study on kineics in the rat's living body when d-α-T3DMA and d-α-T3 were administered An abscissa axis shows time after administration and an ordinate axis shows an amount in each tissue and organ. The d-α-T3DMA was rapidly disappeared from plasma after administration and was transferred to liver. An amount of d-α-T3 in liver was rapidly elevated and the amount was shifted at the same extent of that of a d-α-T3 administered group, and bioavailability of d-α-T3 in liver became 130%. From this, it is supported that d-α-T3DMA is rapidly hydrolyzed in the rat's living body after administration to produce d-α-T3.

FIG. 3 shows the results of study on kinetics in rat's living body when d-γ-T3DMA or d-γ-T3 is administered. An abscissa axis shows time after administration and an ordinate axis shows an amount in each tissue or organ. The d-γ-T3DMA was rapidly disappeared from plasma after administration and was transferred to liver. An amount of d-γ-T3 in liver was rapidly elevated and the amount was shifted significantly highly as compared with a d-γ-T3 administered group, and bioavailability of d-γ-T3 in liver became 213%. In addition, d-γ-T3 in plasma was also rapidly elevated, and it is supported that d-γ-T3 produced in liver is rapidly transferred into plasma. It is understood that d-γ-T3DMA is rapidly hydrolyzed in rat's living body after administration to produce d-γ-T3.

As explained above, according to the tocotrienolcarboxylic acid ester derivative of the present invention, water-solubility is improved and tocotrienol is released rapidly and efficiently in the living body by forming an ester of carboxylic acid having a nitrogen substituent and tocotrienol Test Example 2

Figure 4:
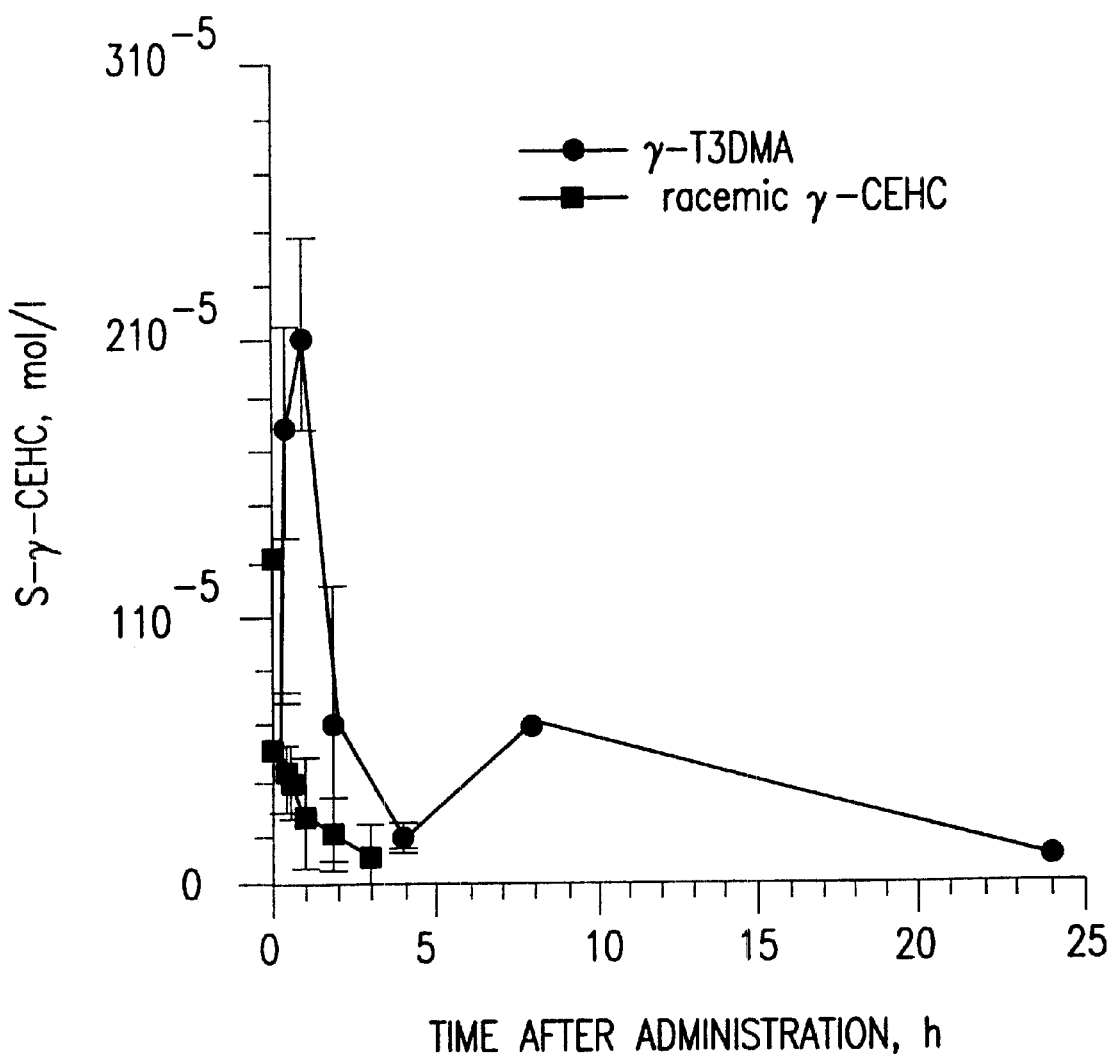
FIG. 4 is a view for explaining the results of study on kinetics in the living body of a rat when d-γ-T3DMA and racemic γ-CEHC are administered.

Maintenance of bioavailability of γ-CEHC by administration of d-γ-tocotrienol N,N-dimethylaminoacetate hydrochloride (γ-T3DMA) into rat vein A SD male rat, 7 weeks old, was used. A solution of γ-T3DMA to be administered was prepared into a d-γ-tocotrienol equivalent 25 mg/ml aqueous solution. The solution was administered intravenously into left femoram vein under slight ether anesthesia, blood was taken from external jugular vein with an injector for tuberculin treated with heparin with time, and plasma was taken after centrifugation. Plasma was stored at −80° C. till HPLC measurement. A γ-CEHC level in plasma was measured by the HPLC method which can fractionally quantitate optical isomers S-γ-CEHC and R-γ-CEHC (Hattori A., Fukushima T., Imai K., Anal. Biochem., 281, 209–215 (2000)). FIG. 4 shows kinetics of S-γ-CEHC in plasma after intravenous administration of γ-T3DMA. R-γ-CEHC was not detected in plasma after administration and only S-γ-CEHC was detected therein. Thus, it was revealed that γ-T3DMA was metabolized into S-γ-CEHC. Here, a S-γ-CEHC level after administration of racemic γ-CEHC is a value at racemic γ-CEHC 1 mg/kg. Table 6 shows pharmacokinetic parameter of S-γ-CEHC in a γ-T3DMA administered group together with data of S-γ-CEHC after administration of racemic γ-CEHC.

S-γ-CEHC in plasma was rapidly elevated after administration of γ-T3DMA and reached Cmax 1 hour after administration. Quantitative bioavailability (F) of a γ-T3DMA administered group was 78.6% using a standard of S-γ-CEHC at administration of racemic γ-CEHC and it was shown that a level of S-γ-CEHC in the living body is efficiently enhanced. Mean Retention Time (MRT) of a γ-T3DMA administered group is 6.64 hr and is an about 7-fold value as compared with MRT 1.00 hr of a racemic γ-CEHC administered group. From the foregoing, it can be understood that γ-T3DMA can enhance the S-γ-CEHC level in the living body and, further, can maintain the S-γ-CEHC level continuously for longer period of time.

TABLE 6

| administered drug | γ-T3DMA | γ-TDMA | racemic γ-CEHC |
|---|---|---|---|
| Dose (μ mol/kg) | 61 | 60 | 3.8 |
| $C_{max}$ (μ mol · ml$^{-1}$) | 19.2 ± 2.98 | 11.5 ± 4.97 | 12.1 ± 1.42 |
| $T_{max}$ (h) | 1 | 1 | 0.003 |
| AUC (μ moL · h · ml$^{-1}$) | 100 ± 14.7 | 128 ± 36.9 | 7.93 ± 4.34 |
| MRT (h) | 6.64 ± 0.50 | 8.32 ± 0.99 | 1.00 ± 0.25 |
| F (%) | 78.6$^{a)}$ | 102$^{b)}$ | 100 |

The pharmacokinetics parameter represents an average of four animals and standard deviation. A dose is γ-T3 equivalent 25 mg/kg. F(%) was obtained by the following equation:
a Obtained by the Following Equation $$F = \frac{AUC^{Plasma}_{S\text{-}\gamma\text{-}CHHC,\gamma\text{-}T3DMA} \cdot D_{racemic\gamma\text{-}CEHC}}{AUC^{Plasma}_{S\text{-}\gamma\text{-}CEHC,racemic\gamma\text{-}CEHC} \cdot D_{\gamma\text{-}T3DMA}} \cdot 100(\%)$$

wherein $AUC_{S\text{-}\gamma\text{-}CEHC,\gamma\text{-}T3DM}^{Plasma}$ and $AUC_{S\text{-}\gamma\text{-}CEHC, racemic\gamma\text{-}CEHC}^{Plasma}$ means AUC of S-γ-CEHC after administration of γ-T3DMA and racemic γ-CEHC, respectively, and $D_{\gamma\text{-}T3DMA}$ and $D_{racemic\ \gamma\text{-}CEHC}$ means a dose of γ-T3DMA and racemic γ-CEHC, respectively.
b Obtained by the Following Equation $$F = \frac{AUC^{Plasma}_{S\text{-}\gamma\text{-}CEHC,\gamma\text{-}TDMA} \cdot D_{racemic\gamma\text{-}CEHC}}{AUC^{Plasma}_{S\text{-}\gamma\text{-}CEHC,racemic\gamma\text{-}CEHC} \cdot D_{\gamma\text{-}TDMA}} \cdot 100(\%)$$

wherein $AUC_{S\text{-}\gamma\text{-}CEHC,\gamma\text{-}TDMA}^{Plasma}$ means AUC of S-γ-CEHC after administration of γ-TDMA, and $D_{\gamma\text{-}TDMA}$ means a dose of γ-TDMA.

Test Example 3

Figure 5:
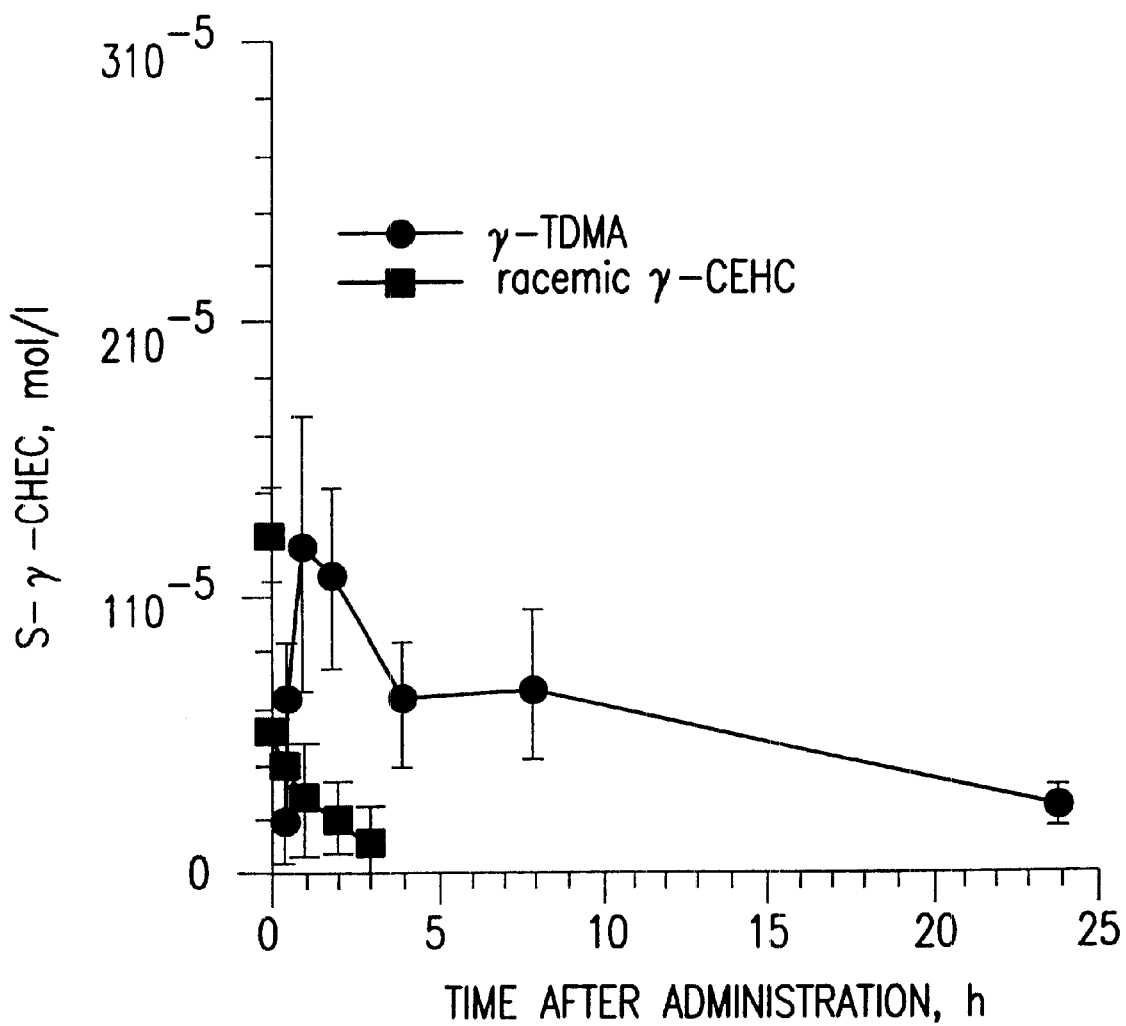
FIG. 5 is a view for explaining the results of study on kinetics in the living body of a rat when d-γ-TDMA and racemic γ-CEHC are administered.

Maintenance of bioavailability of γ-CEHC by administration of d-γ-tocopheryl N,N-dimethylaminoacetate hydrochloride (γ-TDMA) into rat's vein γ-CEHC kinetics in plasma was studied by administering an aqueous γ-TDMA solution into rat's vein according to the same test procedure as those of Test Example 2. The γ-CEHC in plasma was all S-γ-CEHC and R-γ-CEHC was not detected. FIG. 5 shows kinetics of S-γ-CEHC in plasma after administration and the aforementioned Table6 shows pharmacokinetics parameter. A level in plasma was rapidly elevated after administration, reached Cmax after 1 hr, and a S-γ-CEHC level was elevated clearly. Quantitative bioavailability (F) of a γ-TDMA administered group was 102% based on S-γ-CEHC at administration of racemic γ-CEHC, and is approximately the same as that of racemic γ-CEHC administered group. Thus, it was shown that a level of S-γ-CEHC in the living body is efficiently elevated. Mean Retention Time (MRT) of a γ-TDMA administered group was 8.19 hr and was about 8-fold value as compared to MRT 1.00 hr of a racemic γ-CEHC administered group. From this result, it can be understood that γ-TDMA can elevate a S-γ-CEHC level in the living body and continuously maintain a S-γ-CEHC level for a long period of time.

As explained above, according to the delivering agent of the present invention, the water-solubility is improved and γ-CEHC is released in the living body with high bioavailability by preparing into 6-chromanolcarboxylic acid ester having a nitrogen substituent.

Then, the present inventors orally administered a water-soluble 6-chromanolcarboxylic acid ester derivative and studied its bioavailability.

Test Example 4

Figure 6:
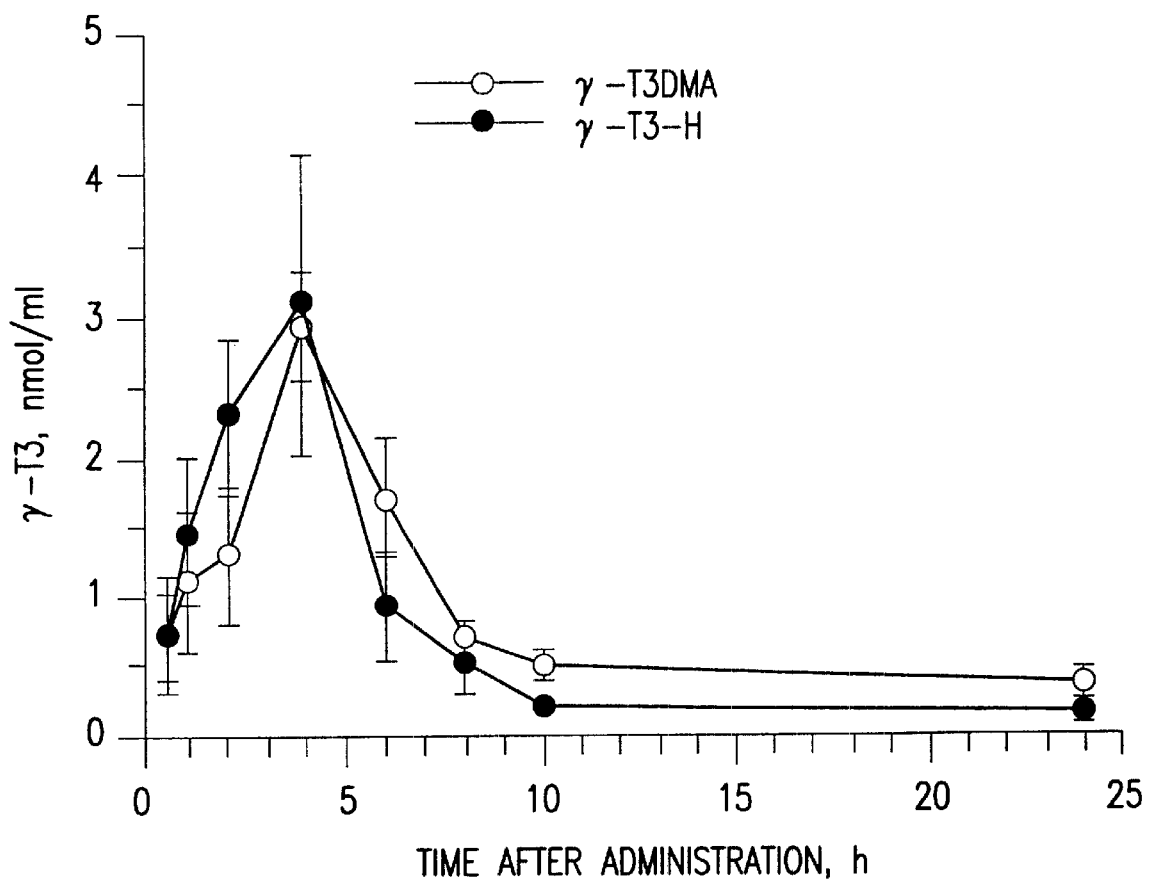
FIG. 6 is a view for explaining the results of study on kinetics in the living body of a rat when d-γ-T3DMA and d-γ-T3-H are administered orally.

Maintenance of bioavailability of γ-tocotrienol by oral administration of d-γ-tocotrienyl N,N-dimethylaminoacetate hydrochloride (γ-T3DMA) in rat SD mail rats (weighing 320–365 g) (3 animals/group) were used by changing a diet to crystal sugar for 16 hours before drug administration. As a γ-T3DMA solution to be administered (γ-T3DMA), its aqueous solution was used and, as a γ-T3 solution to be administered (γ-T3-H), an aqueous solution was used which was solubilized using a surfactnat HCO-10. After a drug solution was orally administered and blood was taken from external jugular vein with time, an amount of γ-T3 in plasma was measured by HPLC. FIG. 6 shows a change in γ-T3 in each plasma with time. In addition, Table 7 shows pharmacokinetics parameter. Both a level of γ-T3DMA in plasma and a level of γ-T3-H in plasma reached Cmax 4 hours after administration and a significant difference was not observed between both administrations by 8 hours after administration. Absolute bioavailability became 20.7±1.4% in the case of γ-T3DMA administration and 17.0±4.4% in the case of γ-T3-H administration and, thus, a significant difference was not observed between both administrations. Like this, it was made clear that γ-T3DMA, requiring no solubilizer HCO-60, functions as an oral agent which can maintain bioavailability equivalent to that of γ-T3 solubilized with HCO-60.

TABLE 7

| administered drug administration method | γ-T3-H (intravenous) | γ-T3-H (oral) | γ-T3DMA (oral) |
|---|---|---|---|
| $C_{max}$ (nmol · ml$^{-1}$) | 175 ± 41 | 3.06 ± 1.06 | 291 ± 0.379 |
| $T_{max}$ (h) | 0.25 | 40 | 4.0 |
| AUC (nmol · h · ml$^{-1}$) | 97 ± 11 | 16.5 ± 4.30 | 20.1 ± 1.40 |
| MRT (h) | 2.00 ± 0.27 | 5.51 ± 0.55 | 7.72 ± 0.35 |
| F (%) | 100 ± 11.3 | 17.0 ± 4.4 | 20.7 ± 1.4 |

The pharmacokinetics parameter represents an average of four animals and standard deviation. A dose was γ-T3 equivalent 25 mg/kg. In addition, F(%) was obtained by the following equation:

$$F = \frac{AUC_{p.o.} \cdot D_{i.v.}}{AUC_{p.o.}^{\gamma-T3-H} \cdot D_{p.o.}} \cdot 100(\%)$$

Obtained by the following equation: wherein $AUC_{po}$ represents AUC of γ-tocotrienol in plasma at oral administration, $ACU_{po}^{r-T3-H}$ represents AUC when γ-T3-H is intravenously administered, $D_{p.o.}$ and $D_{i.v.}$ represents an intravenous dose and an oral dose, respectively.

Test Example 5

Maintenance of bioavailability of γ-tocopherol by oral administration of d-γ-tocopheryl N,N-methylaminoacetate hydrochloride (γ-TDMA) in rat.

Figure 7:
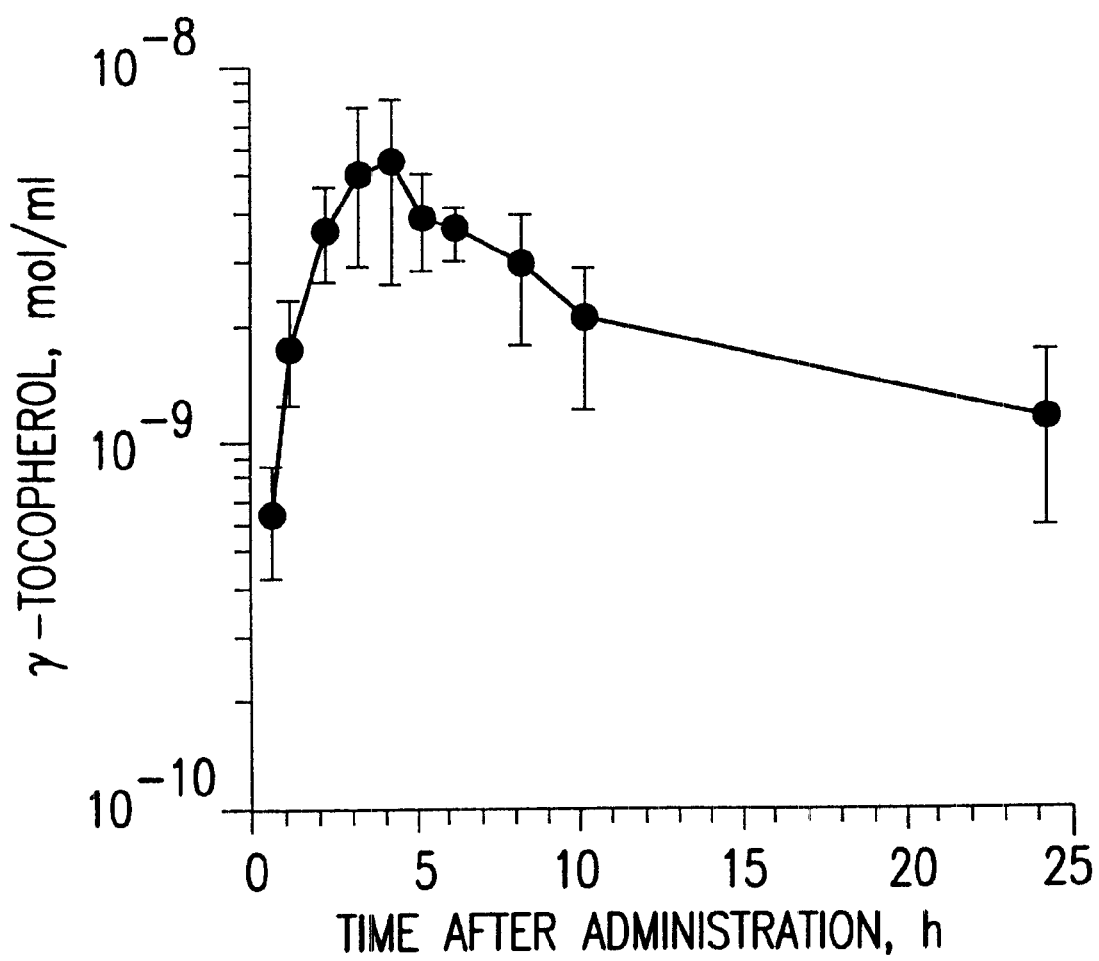
FIG. 7 is a view for explaining the results of study on kinetics in the living body of a rat when d-γ-TDMA is administered orally.

SD male rats (weighing 320–365 g)(3 animals/group) were used by changing a diet to crystal sugar for 16 hours before drug administration. After a γ-TDMA solution to be administered (γ-tocopherol) was orally administered and blood was taken from external jugular vein with time, an amount of γ-tocopherol in plasma was measured by HPLC. FIG. 7 shows a change in γ-tocopherol in plasma with time.

As a result, like the case of the aforementioned tocotrienol, it was shown that maintenance of bioavailability of γtocopherol is possible by administering aqueous 6-chromanolcarboxylic acid ester of the present invention.

As explained above, according to the oral agent of the present invention, bioavailability of tocotrienol, tocopherol or a metabolite thereof can be improved by administering aqueous 6-chromanolcarboxylic acid ester derivative.

What is claimed is:

1. A tocotrienolcarboxylic acid ester derivative represented by the general formula (I):

(I)

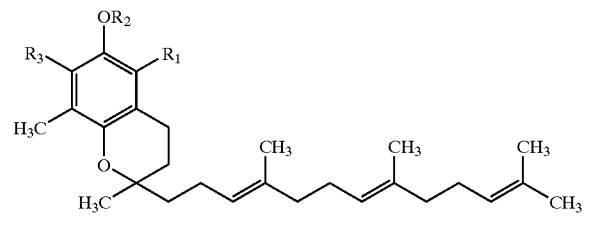

wherein $R_2$ means a carboxylic acid residue having a nitrogen substituent, and $R_1$ and $R_3$ mean a hydrogen atom or a methyl group.

2. The tocotrienolcarboxylic acid ester derivative according to claim 1, wherein the carboxylic acid residue having a nitrogen substituent is at least one selected from the group consisting of residues of amino acid, N-acylamino acid, N-alkylamino acid, N,N-dialkylamino acid, pyridinecarboxylic acid and hydrogen halide salt or alkylsulfonic acid salt thereof.

3. A process for producing a tocotrienolcarboxylic acid ester derivative, which comprises protecting a primary or secondary amino group or an amino group of an amino acid having a hydroxy group or a thiol group on a side chain with a protecting group, and performing a reaction for esterifying the protecting group-coupled amino acid and tocotrienol.

4. A process for producing a tocotrienolcarboxylic acid ester derivative, which comprises performing a reaction for esterifying hydrogen halide salt of N,N-dialkylamino acid and tocotrienol in the presence of an active esterifying reagent.

5. A γ-CEHC delivering agent for releasing 2,7,8-trimethyl-(β-carboxyethyl)-6-hydroxychromane (γ-CEHC) in the living body, which comprises a water-soluble 6-chromanol derivative represented by the general formula (II):

(II)

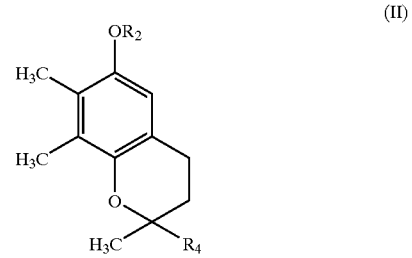

wherein $R_2$ means a carboxylic acid residue having a nitrogen substituent, and $R_4$ means a residue represented by the following formula:

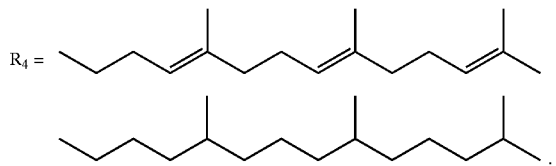

6. An oral agent, which comprises a water-soluble 6-chromanolcarboxylic acid ester derivative represented by the general formula (III):

(III)

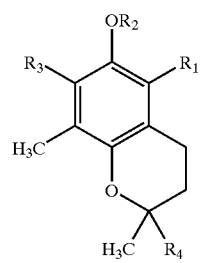

wherein $R_2$ means a carboxylic acid residue having a nitrogen substituent, $R_1$ and $R_3$ mean a methyl group, and $R_4$ is a residue represented by the following formula:

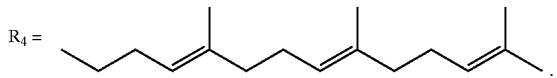

7. A method for improving bioavailability of γ-CEHC, which comprises administering the compound as defined in claim 5 to the living body.

8. An oral agent, which comprises a water-soluble 6-chromanolcarboxylic acid ester derivative represented by the general formula (III):

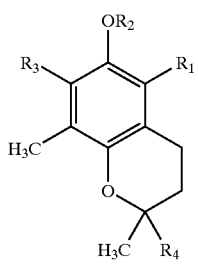

(III)

wherein $R_2$ means a carboxylic acid residue having a nitrogen substituent, $R_1$ means a hydrogen atom and $R_3$ means a methyl group, and $R_4$ is a residue represented by the following formula:

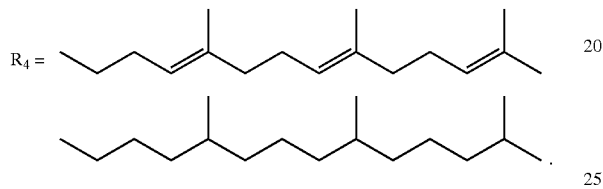

9. An oral agent, which comprises a water-soluble 6-chromanolcarboxylic acid ester derivative represented by the general formula (III):

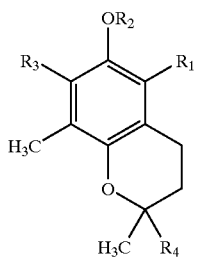

(III)

wherein $R_2$ means a carboxylic acid residue having a nitrogen substituent, $R_1$ means a methyl group, $R_3$ means a hydrogen atom, and $R_4$ is a residue represented by the following formula:

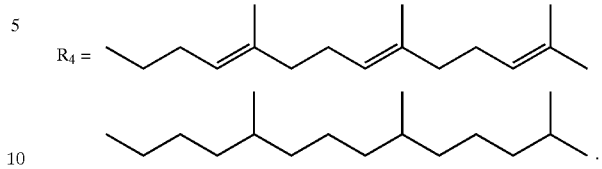

10. An oral agent, which comprises a water-soluble 6-chromanolcarboxylic acid ester derivative represented by the general formula (III):

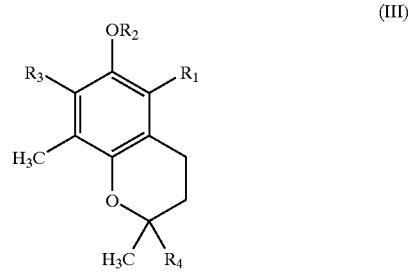

(III)

wherein $R_2$ means a carboxylic acid residue having a nitrogen substituent, $R_1$ and $R_2$ means a hydrogen atom, and $R_4$ is a residue represented by the following formula:

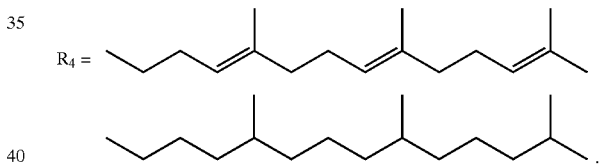

* * * * *

UNITED STATES PATENT AND TRADEMARK OFFICE
CERTIFICATE OF CORRECTION

PATENT NO. : 6,599,933 B2
DATED : July 29, 2003
INVENTOR(S) : Jiro Takata et al.

It is certified that error appears in the above-identified patent and that said Letters Patent is hereby corrected as shown below:

<u>Column 18,</u>
Line 31, please delete "$R_2$" and substitute therefore -- $R_3$ --.

Signed and Sealed this

Ninth Day of December, 2003

JAMES E. ROGAN
*Director of the United States Patent and Trademark Office*